United States Patent [19]

Donofrio

[11] 4,426,450
[45] Jan. 17, 1984

[54] FERMENTATION PROCESS AND APPARATUS

[75] Inventor: David M. Donofrio, Scotts Valley, Calif.

[73] Assignee: Fermentec Corporation, Los Gatos, Calif.

[21] Appl. No.: 340,062

[22] Filed: Jan. 18, 1982

Related U.S. Application Data

[63] Continuation-in-part of Ser. No. 295,566, Aug. 24, 1981, abandoned.

[51] Int. Cl.³ .................. C12N 1/00; C12N 1/16; C12P 7/06; C12M 1/04
[52] U.S. Cl. .................. 435/243; 261/29; 261/124; 261/DIG. 75; 435/161; 435/255; 435/313; 435/316; 435/801; 435/813; 435/819
[58] Field of Search .............. 261/29, 87, 93, 124, 261/DIG. 75; 435/161, 243, 287, 313, 315, 316, 801, 813, 819

[56] References Cited

U.S. PATENT DOCUMENTS

| | | | |
|---|---|---|---|
| 4,139,579 | 2/1979 | Blum | 261/29 |
| 4,211,733 | 7/1980 | Chang | 261/DIG. 75 X |
| 4,244,821 | 1/1981 | Molvar | 261/DIG. 75 X |

*Primary Examiner*—Robert J. Warden
*Attorney, Agent, or Firm*—William B. Walker

[57] ABSTRACT

A method for agitating and mixing a gas with a medium in a closed fermentation vessel comprising recirculating said medium through a venturi jet mixer whereby it is mixed with the gas under high shear conditions to form a mixture of gas saturated medium and a dispersion of small gas bubbles and projected the mixture in the fermentation vessel below the liquid surface level in a plume extending horizontally from the jet mixer, then rising vertically to the liquid surface.

8 Claims, 3 Drawing Figures

FERMENTATION PROCESS AND APPARATUS

CROSS-REFERENCE TO RELATED APPLICATION

This application is a continuation-in-part of U.S. application Ser. No. 295,566, filed Aug. 24, 1981 now abandoned.

BACKGROUND OF THE INVENTION

1. Field of the Invention

In the past, when petroleum was relatively inexpensive, the major portion of industrial ethanol was produced by the catalytic conversion of ethylene. There has been considerable recent interest in the production of industrial ethanol by fermentation as for gasohol production. Prior to that time, any of the developments in alcohol fermentation were made in the beverage alcohol industry, in which concern for maintaining the integrity of desirable flavor components took priority over the optimization of ethanol productivity and yields.

2. Description of the Prior Art

Systems for generating yeast in vessels independently from a main fermentation vessel or chamber has been previously described in U.S. Pat. No. 3,591,454, K. Rosen, *Process Biochemistry*, May, 1978, pp 25, 26 and D. Rose, *Process Biochemistry*, March, 1974, pg 10, for example. U.S. Pat. No. 4,081,367 describes a system for purifying carbohydrate containing waste water by aerobic fermentation with yeast. Air from the tank surface is drawn by a venturi injector into a recycle stream which is injected tangential to the parabolic shaped tank bottom to cause lenticular flow up the tank wall. The waste water is added to the top of the liquid surface. Aeration is limited by horsepower in the inefficient system, and a constantly homogeneous system is not achieved. Thus the fermenation capacity of the system is not achieved.

In copending application Ser. No. 159,953 filed June 16, 1980 and now abandoned, is described an improved system and process for continuously fermenting a carbohydrate substrate (e.g. a fermentable sugar) by inoculation with a microorganism (e.g. yeast) and by use of a small aerobic fermentation vessel and a large main anaerobic fermentation vessel. The substrate feed stream is split between the two vessels. New yeast cells are grown in the aerobic vessel and directed to the anaerobic vessel. A stream concentrated in yeast solids is separated from the alcohol stream removed from the anaerobic vessel and split for recycle to both the aerobic and anaerobic vessels.

The optimum generation of yeast, for example, requires solution of oxygen in the aqueous substrate containing all necessary nutrients at a rate sufficient to replace oxygen consumed by the metabolic process. The rate of yeast generation and hence the production capacity of an aerobic vessel is largely limited by the rate of oxygen solution. Heretofore, oxygen has been introduced by introducing air in fine bubble form, with and without stirring, into the aqueous substrate, and the rate of solution has been primarily a function of bubble surface area and time of bubble-substrate solution contact. Practical means to improve oxygen transfer, for example by using pure oxygen gas, have been too expensive in construction and operation for use in systems for producing industrial grade alcohol or other fermentation products from industrial waste substrates, for example.

SUMMARY OF THE INVENTION AND OBJECTS

In accordance with the present invention, a process and apparatus is provided for dissolving a gas required for fermentation in an aqueous solution of a fermentable substrate at an increased rate. For example, it can be used to increase oxygen solution rates into suspensions of yeast in an aqueous fermentable sugar solution in the aerobic fermentation process and for yeast generation. Substrate solution is removed from the fermentation vessel and passed through a jet mixer means where it is mixed with pressurized air and discharged through a nozzle under high shear conditions, as a plume of air and liquid in the fermentation vessel below the liquid surface thereof. The exit velocity of the air-liquid mixture from the nozzle should be sufficiently high to create a mixing plume, that is, a plume initially traveling in the direction of emergence from the nozzle, preferably horizontally, for a distance and then rising vertically to the liquid surface. The mixing plume causes eddy currents along its edges, forcing a mixing motion throughout the vessel contents, and achieving a constantly homogeneous fermentation medium. In the jet mixer means, the solution is pumped at high velocity through a venturi restriction of circular cross section into a mixing chamber into which is injected air under pressure. The mixture is discharged through a nozzle having a circular cross section into the fermentation vessel contents. The high shear forces in the mixing chamber and nozzle disperse the air in the liquid with greater power and efficiency and with increased solution rate than previously known systems.

It is an object of the invention to provide an improved system for dissolving a gas required for fermentation in a fermentable substrate solution.

It is another object of this invention to provide an improved aerobic fermentation system for generating microorganisms such as yeast whereby through improved efficiency, the size and cost of an aerobic fermentation yeast generating system having a given capacity can be substantially reduced.

It is another object of the invention to provide a total, continuous system incorporating an aerobic fermentation system of the foregoing type capable of producing industrial grade alcohol at relatively high concentrations prior to distillation.

Further objects and features of the present invention will be apparent from the following description taken in conjunction with the appendant drawings.

DETAILED DESCRIPTION OF THE PREFERRED EMBODIMENT

The present system is directed to a method for dissolving a gas more efficiently in an aqueous solution of fermentable substrate to improve the fermentation process. For convenience, the specific description will refer to a sugar, glucose as the fermentable substrate, to yeast as the fermenting microorganism, and to air as the source of oxygen to be dissolved in an aqueous solution of the fermentable substrate. However, it should be understood that this system is also applicable to other fermentation systems in which improved solution of a gas in an aqueous substrate solution is desirable, for example in the production of vinegar with bacteria, enzymes with fungi and antibiotics with mold.

Many different sources may be employed as the carbohydrates substrate, such as products from grain conversion, molasses, and food wastes such as cheese whey. The operating conditions of the system will vary to a great extent depending upon the substrate to be converted.

One important feature of the present invention is the ability to grow the yeast at a rapid rate under optimum aerobic conditions, and to ferment the sugar substrate under optimum anaerobic conditions.

The yeast Saccharomyces Cerevisiae, commonly used in ethanol fermentation, is a facultative anaerobe, which enables it to grow in the presence or absence of oxygen. Under anaerobic conditions, this yeast ferments glucose to yield ethanol and carbon dioxide (catabolic metabolism), and under aerobic conditions it ferments glucose to yield carbon dioxide and new cell mass (anabolic metabolism).

Figure 1:
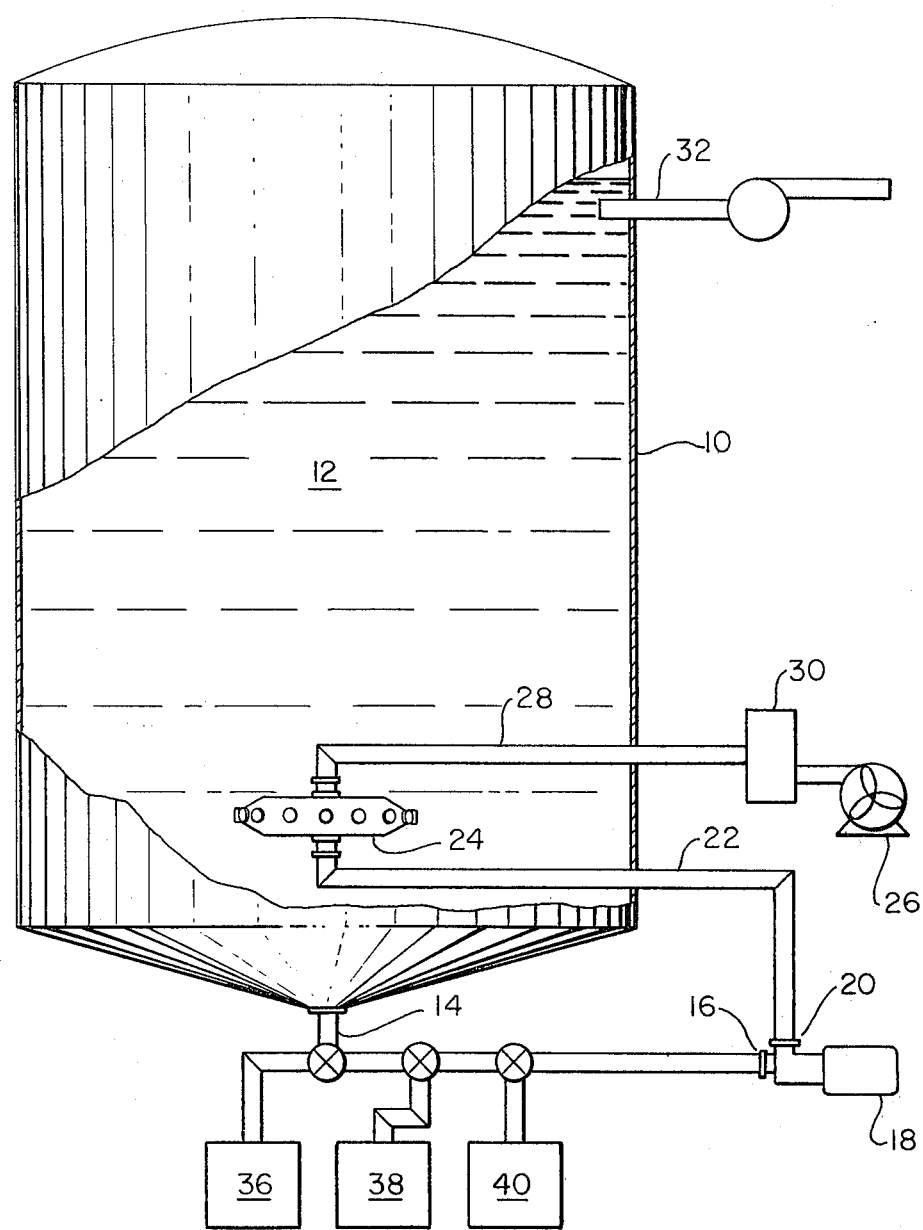
FIG. 1 is a schematic representation of an aerobic fermentation system according to this invention.

Referring to FIG. 1, a schematic representation of an aerobic fermentation system according to this invention is illustrated. Aqueous glucose solution 12 in the closed aerobic fermentation vessel 10 is removed through conduit 14 and passed to the inlet 16 of pump 18. The solution is pumped through outlet 20 and through conduit 22 to the jet mixer 24. Air is supplied to the jet mixer 24 by a blower 26 through conduit 28. The air from blower 26 is preferably filtered through a submicron filter 30 of conventional type to remove undesired microorganisms from the air and prevent contamination of the fermentation system.

A suspension of yeast in substrate solution is removed through conduit 32. Nutrients or other chemicals required for fermentation can be added. For example, nutrients in the form of compounds containing nitrogen, potassium, or phosphorous may be supplied from source 36. Agents for pH adjustments may be supplied from source 38. Also anti-foaming agent may be supplied from source 40. This system can be employed either as a continuous or batch system.

Figure 2:
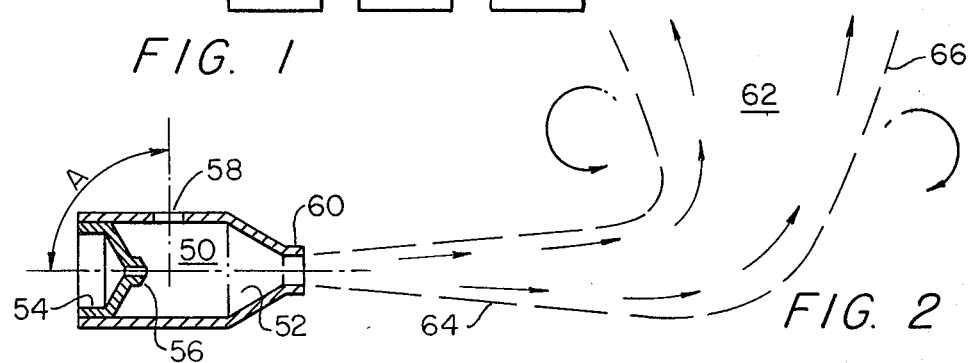
FIG. 2 is a cross sectional representation of a jet mixer means of the type used in the aerobic fermentation system of this invention.

Referring to FIG. 2, a cross-sectional representation of a jet mixer of the type used in the process of this invention, for example in aerobic fermentation, is shown. The jet mixer 50 comprises a mixing chamber 52 for mixing a gas such as air with a liquid such as an aqueous solution of fermentable substrate in which yeast is suspended. The liquid is introduced through port 54 and through venturi restriction 56 into a mixing chamber 52 at a velocity sufficient to create a high shear turbulence in the mixing chamber. The gas is introduced through port 58 into mixing chamber 52. Normal venturi action will draw gas through port 58 into the mixing chamber. However, to provide the requisite volumetric flow, the gas is preferably supplied at above atmospheric pressure to port 58. The gas-liquid mixture exits from the mixing chamber through nozzle restriction 60. Both the venturi restriction and nozzle restriction are preferably circular in cross-section, and the central axis of each is preferably aligned. The gas inlet port is preferably of circular cross section with an axis which forms an angle A of form 45-90 degrees and preferably 90 degrees with the axis of the inlet port 54.

The exit velocity of the air-liquid mixture from the nozzle 60 should be sufficiently high to create a mixing plume 62. The mixing plume comprises a first portion 64 traveling in the direction of emergence from the nozzle, preferably horizontally, and a second portion 66 where it rises vertically to the liquid surface. The mixing plume causes eddy currents along its edges, forcing motion throughout the vessel contents, and achieving a constantly homogeneous fermentation medium.

The optimum dimensions of the ports and mixing chamber of the mixer jet, and the size and ratios of the nozzle restriction 60 to the venturi restriction 56 are dependent upon the respective fluid flows required as well as the physical properties of the respective fluids, i.e., density, viscosity, etc. For aerobic fermentation with aqueous solutions of a fermentable substrate such as glucose and a fermentation microorganism such as a yeast, the diameter ratio of the nozzle restriction 60 to the venturi restriction 56 is greater than 1:1 and preferably from 2:1 to 4:1. The optimum diameter ratio is approximately 2:1.

Referring to FIG. 1, the jet mixer means 24 comprises a plurality of jet mixers, preferably at least three and optimally at least eight, the nozzle axis of each being within 10 degrees and preferably within 5 degrees of the horizontal plane. For use in a fermentation vessel with a height to diameter ratio of 2:1, the optimum jet mixer configuration comprises at least eight jet mixers, the nozzle axis of each extending radially outward in the horizontal plane from a common center which is centrally located in the fermentation vessel. Preferably this common center is on the central axis of the cylindrical fermentation vessel. The jet mixer should be located in the lower 20 to 50 percent of the distance from the vessel bottom surface to the normal liquid surface level and preferably within the lower 15 to 30 percent of said distance.

Figure 3:
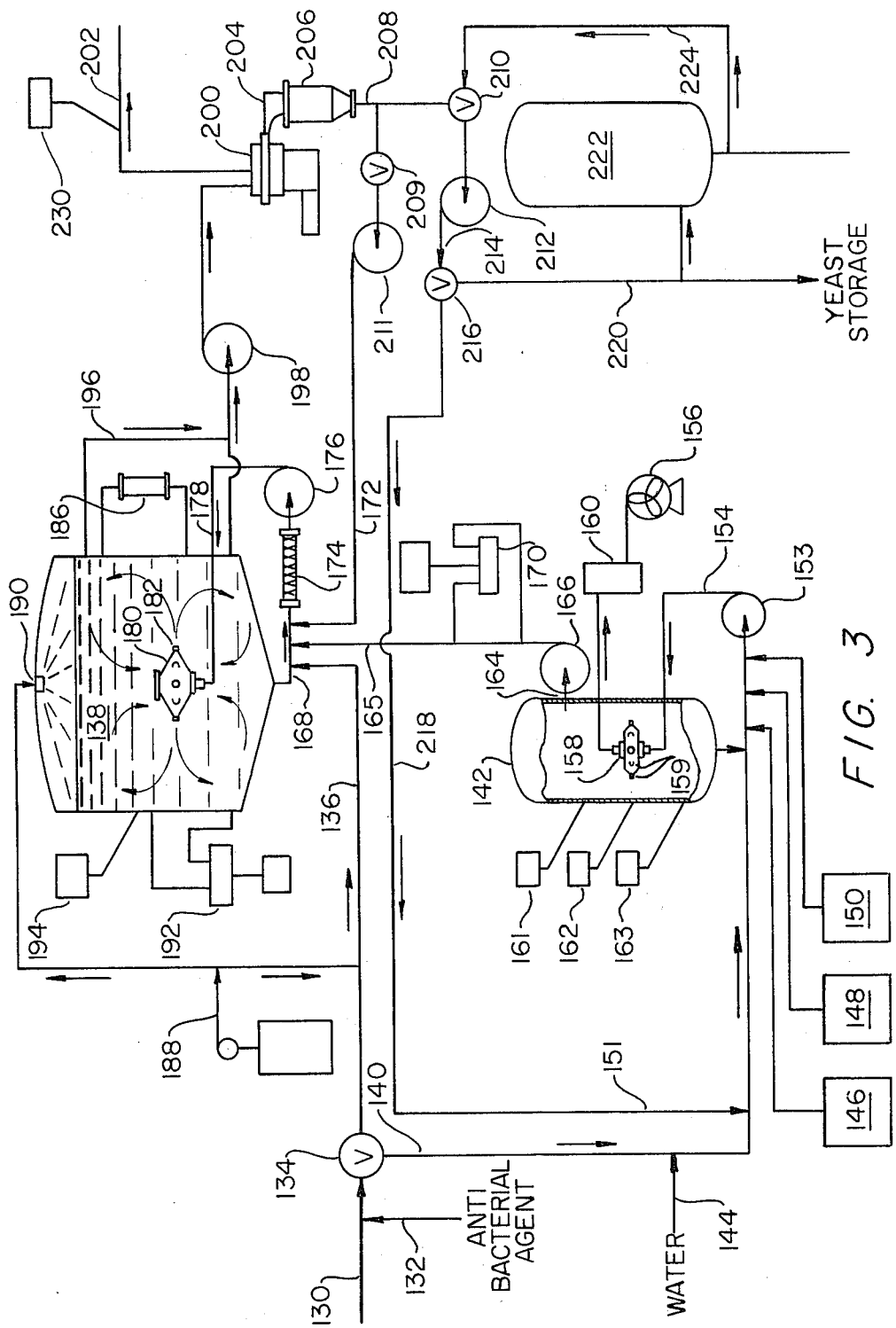
FIG. 3 is a schematic representation of an improved system of this invention for producing industrial grade alcohol by fermentation of industrial wastes containing fermentable sugars.

Referring to FIG. 3, a schematic representation of a continuous fermentation system using the aerobic fermentation apparatus and process of this invention is illustrated. For simplicity of description, the apparatus will be described simultaneously with the method in the order of the flow stream being described.

The substrate, typically containing about 15-30% by weight of fermentable sugar, enters the fermentation system at 130. If desired, an anti-bacterial agent may be added at 132 and thoroughly mixed with the sugar to retard bacterial growth. The substrate flow and anti-bacterial agent may pass through a static in-line mixer (not shown) for a complete mixing. The substrate flow is then directed to a flow diverter control valve 134 which splits the substrate into approximately a 90:10 ratio, with the major or 90% portion being directed in line 136, eventually to anaerobic fermentation vessel 138, while the smaller or 10% fraction is directed in line 140 to aerobic fermentation vessel 142. Typically, the flow rate of substrate to the anaerobic vessel is at least 5 times larger than that to the aerobic vessel.

For yeast production in the aerobic fermentation vessel, the liquid is an aqueous solution containing from 5 to 30 weight percent of a sugar convertible to ethanol by the yeast, the temperature in the fermentation vessel is maintained in the range of from 20° to 40° C., the volume of liquid removed from and returned to the fermentation vessel in one minute exceeds the volume of liquid in the fermentation vessel, and the weight to weight ratio of air to water mixed in the jet mixer is from 1:30 to 1:600. For optimum yeast production in the aerobic fermentation vessel, it is preferable to feed the substrate at an approximately 10% fermentable sugar concentration. Accordingly, assuming the substrate flow at 130 contains about 15–30% fermentable substrate, the stream is diluted by adding water at 144 in sufficient quantity to form a 10% solution, then mixed with recycle liquid from conduit 151.

Certain chemicals may be added to the liquid stream prior to mixing in vessel 142. For example, nutrients in the form of nitrogen, potassium, or phosphorous compounds may be supplied from source 146. Also, antifoaming agent may be supplied from source 148 while acid or base to maintain the proper pH level for maximum yeast growth may be supplied from source 150. The optimum cultivation temperature on the order of 30° C. is maintained in aerobic fermentation vessel 142 using a temperature controller 161, the output of which is used in regulating the temperature of the dilution water 144.

Sufficient oxygen is supplied to aerobic fermentation vessel 142 to maintain aerobic conditions and thus to direct the reaction toward new cell growth rather than fermentation product. This is accomplished by supplying the air to vessel 142 by a blower 156 and introducing the air into the culture liquid in vessel 142 through the jet mixer 158. The air is first filtered as through a submicron filter 160 that effects a high degree of sterility without the necessity of heat sterilization. The dissolved oxygen levels in the culture liquid are preferably maintained at a slight excess of that required by the yeast for growth (e.g., 0.5–2 parts per million) by a dissolved oxygen probe and control 162, the output of which is used in regulating blower 156. The desired pH level of about 3.0 to 5.0 for aerobic growth of yeast is monitored and controlled by a pH controller 163, the output of which is used in feeding the desired amount of acid or base from source 150 to vessel 142 to maintain this level.

The inlet stream is directed through a suitable pump 153 and then through recirculation conduit 154 into an assembly of jet mixers 158 centrally disposed in the vessel with radially disposed jet nozzles 159. Referring to FIG. 2 for representation of an individual jet mixer, the liquid is introduced through port 54 and venturi restriction 56 to cause a high shear, turbulent venturi effect in chamber 52. The incoming air stream passes through port 58 into the mixing chamber 52 where it is intimately contacted with liquid in the high shear developed in the mixing chamber 52 and nozzle 60, saturating the liquid with oxygen and dispersing the air in fine bubbles throughout the liquid as it is directed through nozzle 60.

Referring back to FIG. 3, the air-liquid mixture is directed through nozzles 159, typically at least three and preferably more than six spaced radial nozzles, to pass as high velocity jet streams and provide extremely effective recirculation of the liquid within the tank. The combined substrate, nutrients, and other additives are completely dispersed by introducing them into the jet mixer 158 through recirculation conduit 154. While this type of mixing has been recently described in other applications, it is uniquely effective in mixing the solids and liquids of the aerobic vessel to provide reduced residence times. The principle operation is described in M.G. Mandt and P. R. Bathija, AIChE Symposium Series No. 167, Vol. 73, page 15 (1978), incorporated at this point by reference. Injection into the tank provides all the needed mixing energy. A mixing plume is formed which travels horizontally while spreading through the flow before rising to the surface. Plume momentum is transferred to the surrounding liquid by fine eddy currents formed along the edge of the plume. The eddy currents induce liquid into the plume pattern, forcing tank turnover. In this manner, the mixing effect is felt far beyond the individual jets reaching throughout the vessel.

The fermentation product from vessel 142 is removed from the vessel in line 164, and is directed by pump 166 to line 168 where it is supplied to anaerobic fermentation vessel 138 through the static inline mixer 174, pump 176 and conduit 178. The yeast population in the culture liquid exiting aerobic fermentation vessel 142 is measured by a suitable sensing device 170 such as of the electro-optical type (e.g., a turbidimeter).

Prior to feeding into anaerobic fermentation vessel 138, three separate streams (substrate from line 136, yeast from line 165, and recycling yeast from line 172) are directed into line 168, mixed in static in-line mixer 174, and directed into anaerobic fermentation vessel 138. The details regarding the recycled yeast from line 172 are described below. One advantage of static in-line mixer 174 is that yeast is contacted there with substrate feed at the high concentration at which it is directed to the system, at point 130. It is believed that the short term contact with highly concentrated substrate has a beneficial effect on maintaining the yeast viability for long term operation. This is to be contrasted with directing the yeast to the anaerobic fermentation vessel without such prior contact since the vessel is maintained at a substantially lower substrate content.

A static in-line mixer is a fixed or adjustable arrangement of baffles in a tube or pipe. These baffles divide or re-divide the process stream by a series of elements placed at angles to each other, or by rotational circulation (radial mixing) around the element center. The effect is to completely disperse and intimately contact multi-component flows by the energy in the process stream itself with no moving parts. These systems are generally up to 10 times more efficient than dynamic systems (tank and mixer). A suitable in-line mixer is supplied under the Komax trademark by Komax Systems, Inc., of Long Beach, Calif.

After mixing in in-line mixer 174, the inlet stream for anaerobic fermentation vessel 138 is first directed through a suitable pump 176 and then through line 178 into a manifold assembly 180 centrally disposed in the vessel with radially disposed jet nozzles 182. Pumps 153 and 176 are preferably variable speed recessed impeller pumps with oversized pump cavities to minimize shearing forces on the yeast solids passing through the same. A suitable pump of this type is the Plastonics, Inc. Pyroite recessed impeller pump.

The liquid directed through nozzles 182, typically twelve spaced radial nozzles, exit as high velocity jet streams and provide extremely effective recirculation of the liquid within the tank. While this type of mixing has been recently described in other applications, it is uniquely effective in mixing the solids and liquids of the anaerobic vessel to provide reduced residence times. This system is described above with respect to gas-liquid mixtures in regard to operation of the aerobic fermentation vessel 142, and it is also highly effective with the components in the anaerobic fermentation vessel 138. Injection into the tank provides all the needed mixing energy. A plume is formed which travels horizontally while spreading through the flow before rising to the surface. Plume momentum is transferred to the surrounding liquid by fine eddy currents formed along the edge of the plume. The eddy currents induce liquid into the plume pattern, forcing tank turnover. In this manner, the mixing effect is felt far beyond the individual jets reaching throughout the vessel. A venturi effect is created by the pumped liquid passing through the injection nozzles at high velocity, creating a suction at the open top of the injector, drawing additional tank liquid through the injector for increased mixing action. Tank turnover time is less than one minute.

Variable speed pump 176 provides for a broad range of mixing intensity. Under stable fermentation conditions, the mixing intensity is reduced to minimize energy consumption. However, if the rate of fermentation drops below the desired rate, the pump speed may be increased to intensify the mixing and thereby accelerate the fermentation rate. The suction side of this pump draws the tank contents through the conically shaped bottom of vessel 138 into line 168. The combined flows create an intimate contact with the fresh high-strength substrate flow and yeast. As set out above, this effect maintains the viability of the yeast cells and insures long term operation of the fermentation process without interruption.

A portion of the contents of vessel 138 is passed through a heat exchanger 186 to remove the heat generated by the yeast in the exothermic reaction for conversion of a fermentable substrate to ethanol.

Passing independent portions of the recycled yeast solids stream to the aerobic and anaerobic vessels effects a large size reduction in the aerobic vessel which serves primarily to provide the yeast for the anaerobic vessel. Thus, the anaerobic vessel is many times larger in working volume than the aerobic vessel, say at least 10 times larger.

The liquid level in anaerobic fermentation vessel 138 is typically below the top of the vessel because of the formation of a head space by entrained carbon dioxide gas formed during fermentation. To prevent excessive foaming at the top of the vessel, water is optionally added at 188 through a water spray nozzle 190 at the top of the vessel. In addition, an anti-foam agent may be added with the spray water or in substrate feed line 136.

Under one set of operating conditions, a slight positive pressure is maintained in anaerobic vessel 138 to avoid the intrusion of air from the surroundings. In another mode, anaerobic fermentation is carried out under vacuum to boil off the vapors of ethanol as formed at high concentration (e.g., 30% alcohol). This reduces the cost of subsequent distillation. Vacuum fermentation is particularly effective in the present system in that aerobic fermentation for yeast production can be performed with air rather than under pure oxygen as is required in conventional vacuum fermentation systems where the yeast growth takes place under vacuum.

An electro-optical sensing device 192, suitably of the turbidimeter type, is provided to measure the solids content, and thus the yeast population in the anaerobic fermentation liquid. Although it is illustrated as measuring this level with respect to liquid in the vessel itself, it should be understood that it could be located in the outlet line 196.

In the anaerobic fermentation vessel, the pH level is maintained at the desired level, typically 3.0 to 5.0, by a pH controller 194, the output of which is used to determine settings of a chemical metering system for acid or base (not shown).

The product liquid from anaerobic fermentation vessel 138 is continuously withdrawn though outlet line 196, suitably by a centrifugal or positive displacement feed pump 198, and then is directed to a suitable means for separating the yeast solids from the ethanol product stream. In the illustrated embodiment, a product is directed to a high speed centrifuge 200 which separates the feed stream into an overflow 202 and an underflow 204. Other modes of separation could be employed, such as ultrafiltration, if desired. The underflow from the centrifuge is directed to a yeast discharge tank 206, and through line 208 to valves 209 and 210. A positive displacement sanitary pump 212 continuously removes the yeast slurry from the discharge tank through valve 210 and from there through conduit 214 to flow diverter control valve 216, which splits the stream into line 218 and 220. Another positive displacement sanitary pump 211 continuously removes yeast slurry from the discharge tank 206 through valve 209 and from there to line 172 and to recycle conduit 168. In normal operation, about 90% of this slurry is directed back to the fermentation process by lines 172 and 218, while about 10% is directed to storage vessel 222, from which it is withdrawn in line 224 back into the system when desired. Excess yeast is removed from the system as a usable by-product.

The valves 209, 210 and 216 are set so that 70 to 90 percent of the flow directed back to the fermentation process is returned to the anaerobic fermentation vessel 138 in line 172, while about 5-30% of the flow is returned to the aerobic fermentation vessel in recycle line 218. Under normal operating conditions, the ratio is 95:5.

Means is provided for maintaining the desired yeast population in anaerobic fermentation vessel 138. Such means is in response to sensing device 192 which determines the yeast population as a function of the solids content. When the yeast population and the solids content fall below the optimal level, device 192 senses this low condition. Control valve 216 is adjusted in response thereto to shut the flow in conduit 220 to refrigerated storage tank 222, and if necessary, to reduce or halt flow to the aerobic fermenter 142. Control valve 209 is adjusted so that the flow to anaerobic fermentation vessel 138 is increased up to a maximum where all of the flow passes through line 172. Sensing device 192 detects when the yeast population returns to normal level, and the control valves 209 and 216 are returned to their normal positions.

Means is also provided for maintaining the desired rate of alcohol formation. Should an adverse condition develop in anaerobic fermentation vessel 138 and the alcohol formation fall below its optimum level, this is indicative of a loss of viability of the cells. For this purpose, means 230 is provided for measuring the alcohol level in line 202, suitably an infrared photometer, density meter, or for certain alcohols, a refractive index measuring device. When means 230 senses the reduced alcohol content, a reading is used to regulate the amount of microorganisms directed from aerobic fermentation vessel 142 to anaerobic fermentation vessel 138. In one mode, valve 134 is adjusted to divert more substrate flow to aerobic fermentation vessel 142, and the amount of dilution water 144, nutrients from tank 146, anti-foam agent from tank 148, and acid or base from tank 150, together with the operating speed of pump 166 are correspondingly increased. With this increased substrate flow rate to the aerobic fermentation vessel, the dilution rate is greater than the growth rate of the yeast and a "washout" condition occurs. A sensing device 170 senses a low population in the outflowing liquid, and flow diverter valve 216 is adjusted to cut off the yeast slurry flow to storage 222 and to adjust valve 210 so that additional yeast slurry flows to aerobic fermentation vessel 142. Sensing device 170 is used in regulating such additional flow so that the desired concentration of cells are contained in the outflow from the aerobic fermentation vessel. When the fermentation rate in vessel 138 returns to its optimum level, all flows and valve positions are returned to their normal operating levels.

The sensing device 192 and control valves 209 and 216 can optionally by manual or conventional automatically operating. Similarly sensing means 230, valve 134 and controls for dilution water 144; pumps for nutrient tank 146, anti-foam agent tank 148 and acid or base tank 150; and pump 166 can be optionally selected to be manual or automatically operating. Sensing device 170 and valves 216 and 212 can also be optionally selected for manual or automatic operation. For automatic operation, the sensing devices and valves can be selected from those conventionally available matching systems, in which instance they will be connected by suitable electrical wiring or pneumatic tubing (not shown).

In a typical system, it is preferable to maintain the yeast concentration in the various flow streams at a constant level. If there is any need to increase or decrease the yeast content in the anaerobic fermentation vessel, then the total volume of the various streams to that vessel are increased rather than increasing the yeast concentration only. This is because the growth of yeast cells is sensitive to changes in substrate concentration.

As set out above, a major advantage of separating the yeast growth in the aerobic fermentation vessel is that the conditions for rapid yeast growth are optimized there. Thus, high concentrations of alcohol can be formed in the anaerobic vessel by the addition of the large quantities of newly grown yeast from the aerobic vessel. Another advantage is that by recycling yeast a smaller aerobic vessel may be used together with smaller flows to the anaerobic vessel, thereby decreasing operating and capital costs. Thus, it is desirable to convert essentially all of the substrate in the aerobic vessel to new yeast cells. In that regard, by minimizing the quantities of unconverted substrate flowing from the aerobic to the anaerobic fermentation vessel, e.g., to less than 1% and preferably less than 0.5%, this objective is accomplished.

In a typical instance, the sugar content of the feed stream to the anaerobic fermentation vessel is on the order of 20 to a maximum of 30% sugar by weight. Above this upper limit, the ethanol concentrations produced in the anaerobic fermentation vessel tend to become toxic to the yeast cells. Thus, a typical range of alcohol production is on the order of 8 to 17 volume percent, more specifically about 10 to 12 volume percent. It should be understood that if low sugar containing substrates such as cheese whey are to be fermented, due to the lower sugar concentration (e.g., about 5%), alcohol contents below this level are produced.

Typically, the product stream from anaerobic fermentation vessel 138 includes a residual sugar content on the order of 0.5% sugar. Although typically it is not economical to convert this low sugar content to alcohol, for certain specific applications it would be possible to utilize another anaerobic fermentation vessel to do so.

Another advantage of the present invention is the ability to accomplish a high degree of alcohol conversion in a relatively short retention time. Typically, retention time is dependent upon the growth rate of the yeast cells. In a typical system in accordance with the present invention, less than 10 hours and typically 3 to 6 hours of retention is provided depending upon the substrate. If there are a number of different enzyme systems for each sugar, the fermentation rate and thus total residence time could be as high as 12 hours.

A further disclosure of the nature of the present invention is provided by the following hypothetical example of the practice of the invention. It should be understood that the data disclosed serves only as an example and is not intended to limit the scope of the invention.

EXAMPLE 1

This example illustrates the continuous fermentation process to produce approximately 100 gallons per hour of ethanol from a substrate containing 20% fermentable sugars in the system illustrated in FIG. 3.

A substrate flow of 820 gallons per hour containing 20% fermentable sugar enters the system at line 130. Antibacterial agent (sodium meta-bisulfite) is added at 132 at a level of about 125 ppm. The flow in line 130 is then split at valve 134, a ratio of approximately 90% flow to the anaerobic fermentation vessel in line 136 and 10% to the aerobic fermentation vessel in line 140. The 10% fraction (75 gallons) at line 140 is diluted to about a 10% fermentable sugar level by the addition of 180 gallons per hour of water at 144, to yield a total flow of 154 gallons per hour directed to anaerobic fermentation vessel 142, maintained at 30° C. Nutrients, comprising diammonium phosphate, anti-foam agents (e.g., silicones), and acid or bases as desired are added to fermentation vessel 142. Approximately 315 lbs. per hour of air is supplied to vessel 142 by blower 156, prefiltered through submicron filter 160 for sterilization. The dissolved oxygen levels in the culture liquids are maintained at 0.5 to 2 parts per million. A desired pH level of 3.0 to 5.0 is maintained for the aerobic growth of yeast by a signal to source 150 if this level varies outside this range.

The working volume of aerobic fermentation vessel 142 is about 800 gallons, which effects a four hour residence time at the rate of 154 gallons per hour. At this flow rate, approximately 133 lbs. per hour of fermentable sugars are introduced into vessel 142, which is converted to approximately 67 lbs. per hour of yeast in the four hour residence time. The flow rate from vessel 142 is about 154 gallons per hour, which is directed on line 164, then to static mixer 174 where it is mixed with the 90% substrate fraction (approximately 745 gallons per hour in line 136 from the feed stream and with recycle from line 172 and with the underflow from vessel 138). The recirculating system for the anaerobic fermentation vessel 138 includes a nominal capacity of 100 gallons per minute discharging through nozzles 182. Due to extreme efficient mixing action, tank turnover time is about 6.6 minutes.

About 57 kilo calories per hour of heat is generated by the yeast in conversion of the 1332 pounds of fermentable sugars to 100 gallons of alcohol in the system. This heat is removed by heat exchanger 186.

The working volume of the anaerobic fermentation vessel 138 is approximately 5,000 gallons at a total substrate flow rate of 900 gallons per hour to effect a 4 hour residence time, which allows for the nearly complete conversion of the 1332 pounds of fermentable sugar contained in the 90% fraction into 100 gallons of ethanol. As with the aerobic vessel, the pH level is maintained at a level of 3.0 to 5.0.

The liquid product from the anaerobic vessel is withdrawn at a level toward the top of the vessel, in contrast to the feed toward the bottom of the vessel for optimum mixing. This withdrawn liquid is directed to a high speed centrifuge which separates about 450 lbs. per hour of yeast solids on a dry weight basis, and discharges about 350 gallons per hour of yeast as a 15% dry weight slurry into yeast discharge tank 206. This tank has a capacity of 55 gallons for an effective residence time of about 10 minutes.

Pumps 209 and 212, with a capcity of 350 gallons per hour, continuously remove the yeast slurries from the discharge tank. Approximately 90% of the slurry is directed back to the system in lines 172 and 218, while about 10% is directed to refrigerated yeast storage tank 222 on start-up and 14-day intervals, or is removed as yeast by-product.

The 90% fraction line is split by valves 209, 210 and 216 so that about 95% of this flow (about 300 gallons per hour) is returned to anaerobic fermentation vessel 138, while approximately 5% of the flow (15 gallons per hour) is returned to aerobic fermentation vessel 142.

The desired yeast population in the anaerobic fermentation vessel is maintained in response to the sensing device 192. If there is a variance from this level the systems are adjusted to correct it, as set out above.

In the above system, the liquid or product fraction 202 from the centrifuge 200 contains about 10% ethanol by weight and is directed to distillation at about 900 gallons per hour for further concentration.

Refrigerated yeast storage tank 222 is maintained at about 40° F. and has a storage capacity of about 1400 gallons of yeast slurry, a sufficient quantity to restart the system should fermentation be interrupted and the system drained. The refrigerated yeast is replaced with fresh culture approximately every 14 days.

What is claimed is:

1. An apparatus for carrying out aerobic fermentation in an aqueous solution containing a fermentable carbohydrate and a fermentation microorganism therefor comprising:
   (a) a closed fermentation vessel having cylindrical side walls;
   (b) jet mixing means for mixing solution and air with high shear to form a mixture of aerated solution and small air bubbles and introducing it as a mixing plume of said aerated solution and small air bubbles into said vessel below the liquid surface level thereof in normal operation, the jet mixer means comprising at least three jet mixers, each jet mixer having a nozzle with its central axis extending radially outward from a common center which is centrally located in the fermentation vessel;
   (c) conduit means including pump means communicating with said fermentation vessel below the normal level of the liquid surface thereof and with said jet mixing means for removing solution from the fermentation vessel and introducing it under pressure into the jet; and
   (d) an air supply conduit means communicating with said jet mixing means for supplying air thereto.

2. The apparatus of claim 1 wherein the jet mixing means comprises a jet mixer having:
   (a) a mixing chamber for mixing air and solution under conditions of high shear;
   (b) a restricted venturi port communicating with said mixing chamber and having a circular cross section communicating with said chamber, said venturi port comprising means for introducing recirculated solution into said mixing chamber;
   (c) an air inlet port communicating with said air supply conduit means and with said mixing chamber for introducing air thereto; and
   (d) nozzle means having a circular cross-section communicating with said chamber means, the central axis thereof being substantially aligned with the central axis of the restricted venturi port, and the diameter of the nozzle being greater than the diameter of the venturi port.

3. The apparatus of claim 2 wherein the central axis of the nozzle means forms an angle of less than 10° with the horizontal plane of the fermentation vessel.

4. The apparatus of claim 3 wherein said angle is less than 5°.

5. A process for agitating and dispensing air in a closed system for fermenting yeast in a sugar solution comprising removing liquid from a fermentation vessel and passing the liquid through a jet mixer means and thereafter into the fermentation vessel below the liquid surface level therein, wherein the jet mixer means the liquid is pumped through a venturi restriction into a gas-liquid mixing chamber where it is mixed with air to form a gas-liquid mixture, and the gas-liquid mixture is passed through a plurality of nozzles, each having a central axis extending radially outward from a common center, to form respective radially extending mixing plumes of gas-liquid mixture projected into the fermentation vessel at an angle of within 10° of the horizontal plane, and at a distance from the bottom of the fermentation vessel of from 20 to 50 percent of the total distance from the bottom of the fermentation vessel to the liquid surface level, the velocity of liquid through the venturi restriction and nozzle being sufficient to cause turbulent shear action in the mixing chamber and nozzle, and fine bubble dispersion of gas in the liquid, and the velocity of the air-liquid mixture leaving the nozzle being sufficient to cause a mixing plume, wherein the liquid is an aqueous solution containing from 5 to 30 weight percent of a sugar convertable by a yeast adapted therefor, the temperature in the fermentation vessel in from 20° to 40° C., the volume of liquid removed and returned to the fermentation vessel in one minute exceeds the volume of liquid in the fermentation vessel, and the weight to weight ratio of air to water mixed in the jet mixer means is from 1:30 to 1:600.

6. Apparatus for fermenting a fermentable substrate in an aqueous feed stream by innoculation with a microorganism, said apparatus comprising:
   (a) an aerobic fermentation apparatus comprising:
      (i) a closed fermentation vessel;
      (ii) jet mixing means in the closed fermentation vessel for mixing solution and air with high shear to form a mixture of aerated solution and small air bubbles and introducing it as a mixing plume of said aerated solution and small air bubbles into said vessel below the liquid surface level thereof in normal operation;

(iii) conduit means including pump means communicating with said fermentation vessel below the normal level of the liquid surface thereof and with said jet mixing means for removing solution from the fermentation vessel and introducing it under pressure into the jet; and (iv) an air supply conduit means communicating into said jet mixing means for supplying air thereto;

(b) means connected with the fermentation vessel for introducing a fermentable substrate and microorganism to said aerobic fermentation vessel;

(c) an anaerobic fermentation vessel;

(d) a first conduit means connecting the aerobic fermentation vessel and anaerobic fermentation vessel for directing the reaction product stream, including microorganisms, formed in said aerobic fermentation vessel to said anaerobic fermentation vessel;

(e) means connecting with the anaerobic fermentation vessel for continuously supplying an aqueous feed stream of fermentable substrate to said anaerobic fermentation vessel, whereby a product stream including fermented substrate and a substantial population of microorganism solids are formed;

(f) separation means for separating a microorganism solids stream in said product stream from a fermented substrate stream;

(g) a second conduit means connecting with said anaerobic fermentation vessel and separation means for redirecting the product stream from said anaerobic fermentation vessel to said separation means; and (h) recycle means connecting said separation means and aerobic fermentation vessel and connecting said separation means and anaerobic fermentation vessel for directing one portion of the microorganism solids stream to said aerobic fermentation vessel and another portion to said anaerobic fermentation vessel.

7. The apparatus of claim 6 wherein the jet mixing means comprising the jet mixer having:

(a) a mixing chamber for mixing air and solution under conditions of high shear;

(b) a restricted venturi port communicating with said mixing chamber and having a circular cross section communicating with said chamber, said venturi port comprising means for introducing recirculated solution into said mixing chamber;

(c) an air inlet port communicating with said air supply conduit means and with said mixing chamber for introducing air thereto; and (d) nozzle means having a circular cross section communicating with said chamber means, the central axis thereof being substantially aligned with the central axis of the restricted venturi port, and the diameter of the nozzle being greater than the diameter of the venturi port.

8. A continuous method for fermenting a fermentable substrate in an aqueous feed stream by inoculation with a microorganism, comprising the steps of:

(a) fermenting an aqueous medium of fermentable substrate in the presence of fermenting microorganisms in an aerobic fermentation vessel maintained under essentially aerobic conditions to grow additional microorganisms wherein the contents of the aerobic fermentation vessel are agitated and air is dispersed therein by removing liquid from the aerobic fermentation vessel and passing the liquid through a jet mixer means and thereafter into the aerobic fermentation vessel below the liquid surface level therein, wherein in the jet mixer means the liquid is pumped through a venturi restriction into a gas-liquid mixing chamber where it is mixed with air to form a gas-liquid mixture, and the gas-liquid mixture is passed through at least one nozzle and projected into the fermentation vessel at an angle of within 10° of the horizontal plane, and at a distance from the bottom of the fermentation vessel of from 20 to 50 percent of the total distance from the bottom of the fermentation vessel to the liquid surface level, the velocity of liquid through the venturi restriction and nozzle being sufficient to cause turbulent shear action in the mixing chamber and nozzle and fine bubble dispersion of gas in the liquid, and the velocity of the air-liquid mixture leaving the nozzle being sufficient to cause a mixing plume;

(b) directing an aqueous stream of microorganisms from said aerobic fermentation vessel to an anaerobic fermentation vessel;

(c) continuously flowing to said anaerobic fermentation vessel an aqueous feed constituting the main source of substrate to be fermented from a source which bypasses said aerobic fermentation vessel;

(d) fermenting a portion of said substrate in said anaerobic vessel while maintaining it under essentially anaerobic conditions;

(e) continuously withdrawing from said anaerobic vessel an aqueous product stream of fermented substrate and a substantial population of microorganism solids;

(f) separating said withdrawn stream into a fermented substrate stream and a stream including at least a substantial portion of said microorganism solids; and (g) recycling at least a portion of said separated microorganism solids stream to both said aerobic fermentation vessel and said anaerobic fermentation vessel.

* * * * *